U S010512602B2

United States Patent
Xing et al.

(10) Patent No.: US 10,512,602 B2
(45) Date of Patent: Dec. 24, 2019

(54) CROSSLINKED POLYORGANOSILOXANE AND PERSONAL CARE COMPOSITION CONTAINING SAME

(71) Applicant: Momentive Performance Materials Inc., Waterford, NY (US)

(72) Inventors: Zhimin Xing, Shanghai (CN); Yun Huang, Shanghai (CN); Sigfredo Gonzalez, Danbury, CT (US); Benjamin Falk, Yorktown Heights, NY (US); Anne Dussaud, Tarrytown, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 15/175,211

(22) Filed: Jun. 7, 2016

(65) Prior Publication Data

US 2017/0348220 A1  Dec. 7, 2017

(51) Int. Cl.
| | | |
|---|---|---|
| *A61K 8/891* | (2006.01) | |
| *A61K 8/06* | (2006.01) | |
| *A61Q 1/02* | (2006.01) | |
| *A61Q 5/02* | (2006.01) | |
| *A61Q 5/06* | (2006.01) | |
| *A61Q 5/12* | (2006.01) | |
| *A61Q 17/04* | (2006.01) | |
| *A61Q 19/00* | (2006.01) | |
| *A61Q 19/10* | (2006.01) | |
| *C08G 77/12* | (2006.01) | |
| *C08G 77/20* | (2006.01) | |

(Continued)

(52) U.S. Cl.
CPC ............. *A61K 8/891* (2013.01); *A61K 8/062* (2013.01); *A61K 8/895* (2013.01); *A61Q 1/02* (2013.01); *A61Q 5/02* (2013.01); *A61Q 5/06* (2013.01); *A61Q 5/12* (2013.01); *A61Q 17/04* (2013.01); *A61Q 19/00* (2013.01); *A61Q 19/10* (2013.01); *C08G 77/38* (2013.01); *A61K 2800/437* (2013.01); *A61Q 1/00* (2013.01); *C08G 77/12* (2013.01); *C08G 77/20* (2013.01)

(58) Field of Classification Search
None
See application file for complete search history.

(56) References Cited

U.S. PATENT DOCUMENTS

| | | |
|---|---|---|
| 3,098,833 A | 7/1963 | Solomon |
| 3,445,415 A | 5/1969 | Cekada, Jr. et al. |

(Continued)

FOREIGN PATENT DOCUMENTS

| | | |
|---|---|---|
| EP | 0827983 A2 | 9/1997 |
| WO | 2016014127 A1 | 1/2016 |

OTHER PUBLICATIONS

Shin-Etsu Silicone Global, "Shin-Etsu Personal Care Silicones", https://www.shinetsusilicone-global.com/products/personalcare/products/silicone_gels.shtml (2017).*

(Continued)

*Primary Examiner* — Bethany P Barham
*Assistant Examiner* — Barbara S Frazier
(74) *Attorney, Agent, or Firm* — Joseph S. Ostroff

(57) ABSTRACT

A crosslinked polyorganosiloxane is obtained from the free radical-initiated addition polymerization of polymerizable polyorganosiloxane containing at least two free radical polymerizable groups.

14 Claims, 1 Drawing Sheet

(51) Int. Cl.
*C08G 77/38* (2006.01)
*A61K 8/895* (2006.01)
*A61Q 1/00* (2006.01)

(56) References Cited

U.S. PATENT DOCUMENTS

| | | |
|---|---|---|
| 3,445,420 A | 5/1969 | Kookootsedes et al. |
| 4,248,751 A | 2/1981 | Willing |
| 4,273,634 A * | 6/1981 | Saam ............... C08L 83/04 522/148 |
| 4,288,356 A | 9/1981 | Huebner et al. |
| 4,584,341 A | 4/1986 | Huebner et al. |
| 5,629,388 A | 5/1997 | Himelrick et al. |
| 5,760,116 A | 6/1998 | Kilgour et al. |
| 5,871,761 A | 2/1999 | Kuwata et al. |
| 6,048,910 A | 4/2000 | Furuya et al. |
| 6,147,156 A | 11/2000 | Yamaya et al. |
| 6,534,590 B1 | 3/2003 | Aso et al. |
| 2003/0198655 A1 | 10/2003 | Kaneda et al. |
| 2011/0150818 A1 | 6/2011 | Canfield et al. |
| 2012/0276031 A1 * | 11/2012 | Wei ............... A61K 8/0245 424/63 |
| 2013/0172427 A1 * | 7/2013 | Saxena ............... C09D 183/08 514/772.1 |
| 2017/0165190 A1 | 6/2017 | Fryfogle et al. |
| 2017/0174885 A1 | 6/2017 | Fryfogle et al. |

OTHER PUBLICATIONS

Emmert, "Quantification of the Soft-Focus Effect," Cosmetics and Toiletries, 11, 57-61 (1966).
Zhang et al., "Microemulsion Polymerization of Siloxane with Nonionic Surfactants as Emulsifiers"; Journal of Applied Polymer Science, 89(13): Sep. 23, 2003, 3587-3593.
International Search Report and Written Opinion from PCT/US2017/036044 dated Sep. 20, 2017.

* cited by examiner

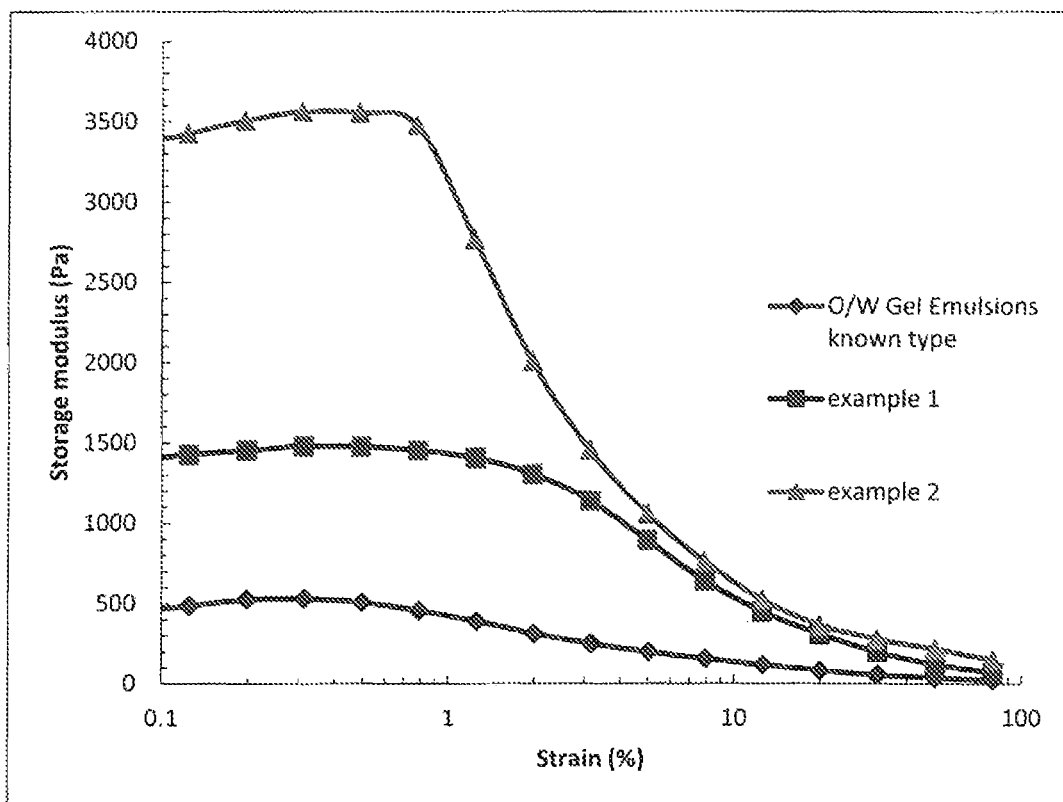

CROSSLINKED POLYORGANOSILOXANE AND PERSONAL CARE COMPOSITION CONTAINING SAME

FIELD OF THE INVENTION

The present invention relates to crosslinked polyorganosiloxanes, their preparation and personal care products containing same.

BACKGROUND OF THE INVENTION

The personal care industry strives to deliver multiple performance products based on mixtures of several components each having performance characteristics important to or desirable in the final formulation. One desirable characteristic is the ability to provide an initial silky feel. This property can be conferred by cyclic siloxanes such as octamethylcyclotetrasiloxane and decamethylcyclopentasiloxane. Although cyclic siloxanes provide the desirable feel characteristics, they are low viscosity and highly flowable liquids. Therefore, they are not readily retained within a formulation preferring rather to separate within a package unit or flow in an uncontrollable manner across the skin upon application.

Known types of polyorganosiloxane gels have been found to deliver the desirable initial silky feel of cyclic siloxanes but unlike the latter, possess viscosities that are high enough to prevent their separation or uncontrollable flow. In addition to providing an initial silky feel, known polyorganosiloxane gels impart to personal care compositions the further desirable quality of producing a smooth silky sensation on dry-down. Such polyorganosiloxane gels are made by the hydrosilylation of ethylenically unsaturated, e.g., vinyl group-containing, polyorganosiloxane by hydrogen polyorganosiloxane in an oil-in-water (O/W) emulsion reaction medium employing a precious metal hydrosilylation catalyst, e.g., a platinum-containing catalyst such as chloroplatinic acid or Karstedt's catalyst (organoplatinum coordination complex). This process produces polyorganosiloxane O/W gel emulsions containing hydrosilylated reaction product(s) exhibiting moderate crosslinking and as a result, moderate levels of storage modulus (G') and relatively high swelling in organic solvent.

SUMMARY OF THE INVENTION

In accordance with the present invention, a crosslinked polyorganosiloxane is provided which comprises at least one member selected from the group consisting of (a) crosslinked polyorganosiloxane O/W gel emulsion obtained from the free radical-initiated addition polymerization under emulsion polymerization reactions conditions of polymerizable polyorganosiloxane I containing ≥2 free radical polymerizable groups and 0 or ≥1 hydrosilyl group(s), or polyorganosiloxane I in the presence of polyorganosiloxane II containing 0 or 1 free radical polymerizable group and ≥1 hydrosilyl group(s), (b) crosslinked polyorganosiloxane O/W gel emulsion (a) which is substantially devoid of precious metal, (c) concentrate of crosslinked polyorganosiloxane O/W gel emulsion (a), and (d) concentrate of crosslinked polyorganosiloxane O/W gel emulsion (b).

Polymerization of polyorganosiloxane I, or polyorganosiloxane I in the presence of polyorganosiloxane II, to provide the foregoing crosslinked polyorganosiloxane O/W gel emulsion may be carried out within an O/W emulsion polymerization reaction medium comprising the polyorganosiloxane(s), water, emulsifier and free radical initiator.

The crosslinked polyorganosiloxane component of the O/W gel emulsion herein and concentrate thereof possess a significantly greater crosslink density than that of a crosslinked polyorganosiloxane/concentrate obtained by the precious metal-catalyzed hydrosilylation process referred to above. Consequently, the crosslinked polyorganosiloxane/concentrate of this invention also possesses significantly greater storage modulus and much reduced swelling by oleophilic materials and organic solvents such as those commonly incorporated in personal care formulations compared with the storage modulus and oil swelling properties of a crosslinked polyorganosiloxane O/W emulsion/concentrate resulting from a precious metal-catalyzed hydrosilylation process.

The greater crosslink density, storage modulus and reduced oil swellability properties that are characteristic of the crosslinked polyorganosiloxane of the invention and its concentrates make them especially desirable components for many kinds of personal care products, e.g., water-based hair care and skin care compositions, to which they impart a heightened cushioning effect, i.e., resistance to spreading by the fingers as such compositions are applied, a sensory effect that consumers are likely to perceive as one of luxuriousness and attributable to product quality.

Personal care compositions containing a crosslinked polyorganosiloxane of the invention after having been applied to hair or skin also tend to exhibit a powdery after feel rather than a film-forming effect which is yet another product characteristic that consumers are likely to find appealing.

A further superior characteristic of the crosslinked polyorganosiloxane herein, and therefore of personal care compositions containing them, is the absence therein of heavy metal compounds, e.g., precious metal catalysts such as Karstedt's catalyst or chloroplatinic acid, which are unavoidably present in crosslinked polyorganosiloxane aqueous gel emulsions/concentrates produced by the aforedescribed hydrosilylation process. The resulting gels that are free of residual metal catalyst typically exhibit better clarity and reduced discoloration compared with their precious metal catalyzed counterparts.

BRIEF DESCRIPTION OF THE DRAWING

FIG. 1 presents in graphical form data comparing the storage moduli (G') of O/W gel emulsions produced by the free radical-initiated addition polymerization of free radical polymerizable group-containing polyorganosiloxane in accordance with the invention and a known type of O/W gel emulsion produced by the hydrosilylation reaction of a silicone hydride fluid and a vinyl silane in the presence of Karstedt's catalyst.

DETAILED DESCRIPTION OF THE INVENTION

In the specification and claims herein, the following terms and expressions are to be understood as indicated.

The singular forms "a," "an," and "the" include the plural, and reference to a particular numerical value includes at least that particular value, unless the context clearly dictates otherwise.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed.

No language in the specification should be construed as indicating any non-claimed element as essential to the practice of the invention.

The terms, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "hydrocarbon group" means any hydrocarbon from which one or more hydrogen atoms has been removed and is inclusive of alkyl, alkenyl, alkynyl, cyclic alkyl, cyclic alkenyl, cyclic alkynyl, aryl, aralkyl and arenyl groups and is inclusive of hydrocarbon groups containing at least one heteroatom.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

The term "heteroatom" means any of the Group 13-17 elements except carbon and includes, for example, oxygen, nitrogen, silicon, sulfur, phosphorus, fluorine, chlorine, bromine and iodine.

In one embodiment, hydrocarbon group(s), where present, contain up to 60 carbon atoms, in another embodiment up to 30 carbon atoms and in yet another embodiment up to 20 carbon atoms.

Useful hydrocarbon groups include alkyl groups examples of which are methyl, ethyl, n-propyl, isopropyl, n-butyl, isobutyl, tert-butyl, n-pentyl, isopentyl, neopentyl and tert-pentyl; hexyl such as n-hexyl; heptyl such as n-heptyl; octyl such as n-octyl, isooctyl and 2,2,4-trimethylpentyl; nonyl such as n-nonyl; decyl such as n-decyl; and cycloalkyl, such as cyclopentyl, cyclohexyl, cycloheptyl and methylcyclohexyl. Examples of alkenyl groups include vinyl, propenyl, allyl, methallyl, cyclohexenyl, norbornenyl, ethylnorbornenyl, ethylidenyl norbornane, ethylidene norbornyl, ethylidenylnorbornene and ethylidene norbornenyl. Examples of alkynyl groups include acetylenyl, propargyl and methylacetylenyl. Examples of aryl groups include phenyl, naphthyl; o-, m- and p-tolyl, xylyl, ethylphenyl and benzyl.

The terms and expressions "hydrosilyl", "silanic hydrogen", "hydride", "silicone hydride", "SiH", are understood in the organosiloxane art to be used interchangeably and to designate polyorganosiloxanes that contain one or more hydrogen atoms bonded directly to silicon.

The term "emulsion" as used herein shall also be understood to include "microemulsion".

As stated above, polyorganosiloxane I from which the crosslinked polyorganosiloxane component of the O/W gel emulsion herein is obtained contains at least two groups that are polymerizable, i.e., crosslinkable, under free radical addition polymerization reaction conditions, e.g., $\geq 2$ and $\leq 5000$ free radical polymerizable groups, more specifically $\geq 2$ and $\leq 1000$ free radical polymerizable groups and still more specifically $\geq 2$ and $\leq 500$ free radical polymerizable groups. This requirement is satisfied by functional groups containing ethylenic unsaturation, such groups being directly bonded to a silicon atom. In addition to its free radical polymerizable groups, polyorganosiloxane I may contain one or more hydrosilyl groups, e.g., $\geq 1$ and $\leq 500$ hydrosilyl groups, more specifically $\geq 1$ and $\leq 100$ hydrosilyl groups and still more specifically $\geq 1$ and $\leq 50$ hydrosilyl groups.

In one embodiment, polyorganosiloxane I is of the general formula:

$$M_a M^H{}_b M^V{}_c M''{}_d M^*{}_e D_f D^H{}_g D^V{}_h D''{}_i D^*{}_j T_k T^H{}_l T^V{}_m T''{}_n T^*{}_o Q_p \qquad I$$

wherein
$M = R^1 R^2 R^3 SiO_{1/2}$;
$M^H = R^4 R^5 HSiO_{1/2}$;
$M^V = R^6 R^7 R^8 SiO_{1/2}$;
$M'' = R^9 R^{10} R^{22} SiO_{1/2}$;
$M^* = R^{11} R^{12} R^{23} SiO_{1/2}$;
$D = R^{13} R^{14} SiO_{2/2}$;
$D^H = R^{15} HSiO_{2/2}$;
$D^V = R^{16} R^{17} SiO_{2/2}$;
$D'' = R^{18} R^{22} SiO_{2/2}$;
$D^* = R^{19} R^{23} SiO_{2/2}$;
$T = R^{20} SiO_{3/2}$;
$T^H = HSiO_{3/2}$;
$T^V = R^{21} SiO_{3/2}$;
$T'' = R^{22} SiO_{3/2}$;
$T^* = R^{23} SiO_{3/2}$; and,
$Q = SiO_{4/2}$ in which $R^1$, $R^2$, $R^3$, $R^4$, $R^5$, $R^7$, $R^8$, $R^{13}$, $R^{14}$, $R^{15}$, $R^{17}$ and $R^{20}$ each independently is a monovalent hydrocarbon group of up to 60 carbon atoms, more specifically of up to 30 carbon atoms and still more specifically of up to 20 carbon atoms; $R^6$, $R^{16}$ and $R^{21}$ each independently is a free radical polymerizable group, more specifically an ethylenically unsaturated group; $R^9$, $R^{10}$ and $R^{18}$ each independently is a monovalent hydrocarbon group of up to 60 carbon atoms, more specifically of up to 30 carbon atoms and still more specifically of up to 20 carbon atoms, or $R^{22}$; each $R^{22}$ is independently a monovalent alkoxy group of up to 60 carbon atoms, more specifically of up to 30 carbon atoms and still more specifically of up to 20 carbon atoms, and optionally containing at least one ionic group, e.g., cationic, anionic and/or zwitter ionic group such as carboxylate, sulfate, sulfonate, quarternized amide, sulfobetaine, and the like; $R^{11}$, $R^{12}$ and $R^{19}$ each independently is a monovalent hydrocarbon group of up to 60 carbon atoms, more specifically of up to 30 carbon atoms and still more specifically of up to 20 carbon atoms, or $R^{23}$; each $R^{23}$ is a divalent alkylene group $R^{24}$ of from 3 to 6 carbon atoms to which is bonded one or more alkyleneoxy groups having a total of from 2 to 200 carbon atoms, more specifically of up to 100 carbon atoms and still more specifically of up to 50 carbon atoms, optionally terminated by hydrogen, an alkyl group of up to 20 carbon atoms, more specifically 8 of up to 10 carbon atoms and still more specifically of up to 4 carbon atoms, or at least one ionic group, e.g., cationic, anionic or zwitterionic group such as carboxylate, sulfate, sulfonate, quarternized amide, sulfobetaine, and the like; and, subscripts a, b, c, d, e, f, g, h, i, j, k, l, m, n, o and p each independently is 0 or a positive number subject to the provision that c+h+m≥2, e.g., ≥2 and ≤5000, more specifically ≥2 and ≤1000 and still more specifically ≤2 and ≥500, and a+b+d+e+f+g+i+j+k+l+n+o+p is 0 or ≥1, e.g., ≥1 and ≤3000, more specifically ≥2 and ≤2000 and still more specifically ≥2 and ≤1000.

In one embodiment, at least one of free radical polymerizable groups $R^6$, $R^{16}$ and $R^{21}$ is selected from the group consisting of:

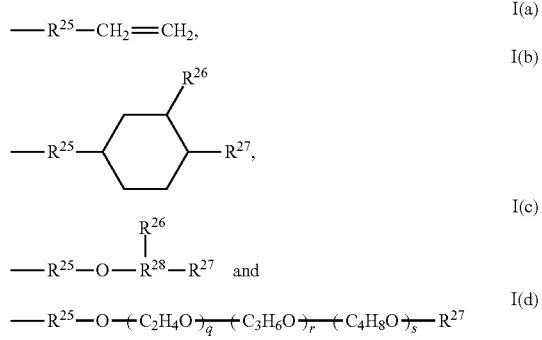

in which each $R^{25}$ independently is a divalent hydrocarbon group of up to 20 carbon atoms, and more specifically of up to 10 carbon atoms, optionally containing one or more heteroatoms; $R^{26}$ and $R^{27}$ each independently is an ethylenically unsaturated free radical polymerizable, i.e., crosslinkable, group such as alkenyl, vinyl, methallyl, acrylate, acrylamide, methacrylamide, acrylyl, and the like; $R^{28}$ is a trivalent hydrocarbon group of up to 20 carbon atoms, and more particularly of up to 10 carbon atoms, optionally containing one or more heteroatoms; and, subscripts q, r and s each independently is 0 or a positive number subject to the requirement that q+r+s≥1 and ≤60, more specifically ≥1 and ≤30 and still more specifically ≥1 and ≤20.

Where polyorganosiloxane I contains at least one group of formulas I(b), I(c) and/or I(d), at least one of groups $R^{26}$ and $R^{27}$ therein can be a group of the general formula:

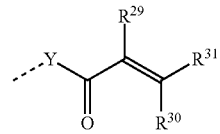

in which Y is absent or is an $R^{25}$ group as previously defined and $R^{29}$, $R^{30}$ and $R^{31}$ each independently is hydrogen or a monovalent hydrocarbon group of up to 20 carbon atoms.

Where polyorganosiloxane I contains two or more $M^V$, $D^V$ and/or $T^V$ unsaturated moieties but no hydrosilyl-containing moieties $M^H$, $D^H$ or $T^H$, i.e., where c+h+m≥2 and b+g+l=0, its polymerizate will possess crosslinks resulting entirely from the addition polymerization of unsaturated moieties. However, where polyorganosiloxane I, in addition to its unsaturated moieties, contains one or more hydrosilyl-containing moieties $M^H$, $D^H$ and/or $T^H$, i.e., c+h+m≥2 and b+g+l≥1, the polyorganosiloxane I polymerizate will not only possess crosslinks resulting from the addition polymerization of unsaturated moieties but also crosslinks resulting from the hydrosilylation of unsaturated moieties by hydrosilyl moieties.

Where polymerizable polyorganosiloxane I lacks any hydrosilyl group-containing moiety $M^H$, $D^H$ or $T^H$, i.e., where b+g+l=0, it is within the scope of the invention to include within the O/W emulsion reaction medium polyorganosiloxane II which is defined the same as for polyorganosiloxane I but with the limitation that polyorganosiloxane II contains 0 or 1 unsaturated group-containing $M^V$, $D^V$ or $T^V$ moiety, i.e., c+h+m is 0 or 1, and at least one hydrosilyl-containing moiety $M^H$, $D^H$ and/or $T^H$, i.e., b+g+l≥1, e.g., ≥1 and ≤500, more specifically ≥1 and ≤100 and still more specifically ≥1 and ≤50, it being understood that subject to this limitation, each of groups $R^1$-$R^{24}$ and subscripts l-p of polyorganosiloxane II are selected independently of the like-designated groups and subscripts of polyorganosiloxane I. In this embodiment, in addition to crosslinks resulting from the free radical initiated addition polymerization of unsaturated group-containing moieties $M^V$, $D^V$ and/or $T^V$ of polyorganosiloxane I, the polymerizate of polyorganosiloxane I will also possess crosslinks resulting from the hydrosilylation of unsaturated groups of polyorganosiloxane I by hydrosilyl-containing groups of polyorganosiloxane II.

It is desirable that in all embodiments of the O/W gel emulsion herein the emulsion reaction medium be devoid of precious metal hydrosilylation reaction catalyst, e.g., of the platinum-containing type, where the resulting crosslinked polyorganosiloxane O/W gel emulsion or crosslinked polyorganosiloxane isolated therefrom is intended to be incorporated in a personal care product in view of the previously stated propensity of such catalysts to cause discoloration or decreased clarity.

Examples of polyorganosiloxane I in which c+h+m is ≥2 and b+g+l is 0 or ≥1 include formula I(e):

$$M^V{}_c D^V{}_f D^V{}_h M_{2-c} \qquad \text{I(e)}$$

wherein $M^V$, D, $D^V$ and M are as previously defined and subscripts c, f and h are 0 or a positive number subject to the limitation that f is 0 to 2000, more specifically 10 to 1000 and still more specifically 10 to 500, h is 0 to 500, more specifically 0 to 100 and still more specifically 0 to 50, and c is 0 to 2, provided c+h is 2 to 500, more specifically 2 to 100 and still more specifically 2 to 50; formula I(f):

$$M^V_c D_f D^V_h M_{2-c}$$  I(f)

wherein $M^V$, D, $D^V$ and M are as previously defined and subscripts c, f and h are 0 or a positive number subject to the limitation that f is 0 to 2000, more specifically 10 to 1000 and still more specifically 10 to 100, h is 0 to 500 and more specifically 0 to 100, and c is 0 to 50, provided that c+h is 2 to 500, more specifically 2 to 100 and still more specifically 2 to 50; formula II:

$$M^V_c Q_p$$  I(g)

wherein $M^V$ and Q are as previously defined and subscripts c and p are 0 or a positive number subject to the limitation that c is ≥1, more specifically ≥2 and still more specifically ≥3, and p is ≥1, more specifically ≥2 and still more specifically ≥3, provided c+p is 2 to 20, more specifically 2 to 10 and still more specifically 2 to 6; formula I(h):

$$M^H_b M^V_c D_f D^H_g D^V_h M_{2-b}$$  I(h)

wherein $M^H$, $M^V$, D, $D^H$, $D^V$ and M are as previously defined and b, c, f, g and h are 0 or a positive number subject to the limitation that f is 1 to 1000, more specifically 10 to 300 and still more specifically 10 to 100, b is 0 or 1 and c is 0 to 2, provided, b+g is 1 and c+h is 2 to 500, more specifically 2 to 100 and still more specifically 2 to 50; and, formula II:

$$D_f D^V_h$$  I(i)

wherein D and $D^V$ are as previously defined and subscripts f and h are 0 or a positive number subject to the limitation that f+h is 3 to 8, more specifically 3 to 6 and still more specifically 3 to 5.

In polymerizable polyorganosiloxanes I(e)-I(i), the $M^V$ and $D^V$ moieties advantageously containing vinyl, allyl, methallyl, acrylate and/or alkacrylate groups with vinyl-containing groups being preferred. Specific polyorganosiloxanes I of these types that may advantageously be used to provide the crosslinked polyorganosiloxane O/W gel emulsion herein include 1,1,3,3,3,7-hexamethyl-5, 7-divinylcyclo tetrasiloxane, 1,3,5,7-tetravinyl-1,3,5,7-tetramethylcyclotetrasiloxane, RTV644 which is a trade name for a vinyl terminated polysiloxane with a vinyl content of 0.26 meq/g, RTV646 which is a trade name for a vinyl terminated polysiloxane with a vinyl content of 0.034 meq/g, RTV609 which is a trade name for a vinyl terminated polysiloxane with with a vinyl content of 0.064 meq/g, SL5000 which is a trade name for a vinyl terminated polysiloxane with a silicone gum with a vinyl content of 0.09% vinyl, SL6700 which is a trade name for a vinyl terminated vinyl pendant polysiloxane, Silopren™ VS-S which is a trademarked name for a vinyl terminated vinyl pendant polysiloxane with a vinyl content of 0.024 meq/g, SE31 which is a trade name for a vinyl functional silicone resin, branched vinyl siloxanes such as the trade name product SL7000, phenyl-modified vinyl fluids such as the trade name product RTV652A, and vinyl resins such as the trade name product 88302, all from Momentive Performance Materials Inc.

Examples of polyorganosiloxane II, i.e., wherein c+h+m is 0 or 1 and b+g+l is ≥1, include formula II(a):

$$M^H_b D_f D^H_g M'_{2-b}$$  II(a)

wherein $M^H$, D, $D^H$ and M' are as previously defined and b, f and g are 0 or a positive number subject to the limitation that f is 10 to 50, more specifically 10 to 30 and still more specifically 10 to 25, g is 0 to 50, more specifically 1 to 30 and still more specifically 2 to 10 and b is 0 to 2, provided, b+g is 1 to 100, more specifically 1 to 32 and still more specifically 2 to 12; formula II(b):

$$M^H_b D_f D^H_g M'_{2-b}$$  II(b)

wherein $M^H$, D, D*, $D^H$ and M are as previously defined and subscripts b, f, g and j are zero or a positive number subject to the limitation that b is 0 to 2, g is 0 to 50, more specifically 1 to 30 and still more specifically 2 to 10, j is 0.1 to 10, more specifically 0.1 to 8 and still more specifically 0.1 to 6 and f is 0 to 500, more specifically 10 to 150 and still more specifically 10 to 125, provided, b+g is 1 to 100, more specifically 1 to 32 and still more specifically 2 to 12; formula II(c):

$$M^H_b Q_p M'_{2-b}$$  II(c)

wherein $M^H$, Q and M are as previously defined and b and p are 0 or a positive number subject to the limitation that b is ≥1, more specifically ≥2 and still more specifically ≥3, and p is ≥1, more specifically ≥2 and still more particularly ≥3, provided, b+p is 2 to 20, more specifically 2 to 10 and still more specifically 2 to 6; formula II(d):

$$M^H_b D_f D''_i D^H_g M_{2-b}$$  II(d)

wherein $M^H$, D, D'', $D^H$ and M are as previously defined and b, f, i and g are 0 or a positive number subject to the limitation that f is 10 to 50, more specifically 10 to 40 and still more specifically 10 to 35, i is 0 to 20, more specifically 1 to 12 and still more specifically 1 to 8 and b is 0 to 2, provided, b+g is 1 to 100, more specifically 1 to 14 and still more specifically 1 to 10; formula II(e):

$$M^H_b M^V_c D_f D^H_g D^V_h M_{2-b}$$  II(e)

wherein $M^H$, $M^V$, D, $D^H$ and M are as previously defined and b, c, f, g and h are 0 or a positive number subject to the limitation that f is 1 to 300, more specifically 10 to 30 and still more specifically from 10 to 25, provided, b+g is ≥1, more specifically ≥2 and still more specifically ≥3 and c+h is 0 or 1; and, $$D_f D^H_g D^V_h$$  II(f)

wherein D, $D^H$ and $D^V$ are as previously defined and f, g and h are 0 or a positive number subject to the limitations that f+g+h is 3 to 7 and more specifically 3 to 5 and h is 0 or 1.

Specific polyorganosiloxanes II include $M^H_b D_f D^H_g$ wherein $M^H$, D, $D^H$ and subscripts b, f and g are as previously defined, e.g., TSF484, SilForce SL4380, SilForce SL4320 and SilForce SL4330 (Momentive Performance Materials Inc.), 1,3,5,7-methylcyclotetrasiloxane.

The ratio of total free radical polymerizable groups of polymerizable polyorganosiloxane I, and where present, of polyorganosiloxane II, to total hydrosilyl groups of polyorganosiloxane II, and where present, of polyorganosiloxane I, should be at least 1 and advantageously at least 2. On a weight basis, the weight ratio of total polyorganosiloxane I to total optional polyorganosiloxane II can vary widely, e.g., in a first embodiment from 100:0 to 1:99, in a second embodiment from 100:0 to 50:50 and in a third embodiment from 100:0 to 80:20.

The number average molecular weight ($M_n$) of polyorganosiloxane(s) I and II as measured by NMR can vary widely, e.g., in one embodiment from 100 to 500,000, in another embodiment from 100 to 100,000 and in yet another embodiment from 100 to 50,000.

The viscosities of polyorganosiloxanes I and II can also vary through broad limits. For example, in a first embodiment, polyorganosiloxane I can have a viscosity as measured by Brookfield Rotary Viscometry of from 0.0002 to 1000 Pa·s, and in a second embodiment of from 0.0002 to 10 Pa·s, and polyorganosiloxane II can have a viscosity of from 0.002 to 50 Pa·s in a first embodiment and from 0.002 to 10 Pa·s in a second embodiment.

In most cases, polyorganosiloxanes I and II will be present within the O/W emulsion polymerization reaction mixture at the onset of polymerization. However, it is within the scope of the invention to commence polymerization of polyorganosiloxane I alone and only thereafter but before completion of polymerization of polyorganosiloxane I to introduce optional polyorganosiloxane II into the emulsion reaction medium whereby as-yet unreacted $M^V$, $D^V$ and/or $T^V$ moieties present in polyorganosiloxane I will undergo hydrosilylation by $M^H$, $D^H$ and/or $T^H$ moieties present in polyorganosiloxane II. It is therefore to be understood that in the case of delayed addition of polyorganosiloxane II to polyorganosiloxane I while a portion of the latter is undergoing polymerization, the expression "polyorganosiloxane I" includes partially polymerized polyorganosiloxane I containing one or more as-yet unreacted $M^V$, $D^V$ and/or $T^V$ moieties. Delayed addition of polyorganosiloxane II to polyorganosiloxane I can be advantageous when preparing an interpenetrating polymer network (IPN) or a core-shell structure.

Free radical-initiated polymerization of polymerizable polyorganosiloxane I and hydrosilylation of polyorganosiloxane I by polyorganosiloxane II where utilized can be carried out in an O/W emulsion polymerization reaction medium employing conventional or otherwise known emulsion polymerization procedures.

In these polymerization procedures, the dispersed oil phase of the emulsion reaction mixture which includes polymerizable polyorganosiloxane I, optional polyorganosiloxane II and optional organic solvent and/or swelling agent (compatibilizer), and the continuous aqueous phase of the emulsion reaction medium which includes water and water-soluble or water-miscible components such as emulsifier, free radical initiator and optional components such as stabilizers, co-stabilizers, chain transfer agents, and the like, can be present in conventional or otherwise known amounts. In general, the oil phase can constitute from 1 to 80, and advantageously from 30 to 70, weight percent of the emulsion polymerization reaction medium with the aqueous phase making up the balance.

The amount of polyorganosiloxane I, or as the case may be, mixture of polyorganosiloxanes I and II, as a percentage of the total weight of the oil phase can vary widely, e.g., in one embodiment from 10 to 100 weight percent and in a second embodiment from 20 to 80 weight percent.

Solvents and/or swelling agents (compatibilizers), generally those having melting points below 80° C. and preferably below 50° C., can be incorporated in the oil phase of the emulsion polymerization reaction medium. Suitable solvents/swelling agents include hydrocarbons such as isodecane, hexadecane and squalane; triglycerides such as caprylic triglyceride; esters such as cetyl palmitate and isopropyl myristate; ethers such as dipropylene glycol butyl ether, polyhydric alcohols such as hexadecanol and organic acids such as hexadecenoic acid; and, non-reactive polyorganosiloxanes, e.g., methicones such as octyl methicone, dimethicone, alkyl dimethicone, phenyl dimethicone, amino dimethicone, trimethylsiloxysilicate and polymethylsilsesquioxane. Such solvents/swelling agents can represent up to 95 weight percent of the oil phase of the O/W emulsion reaction medium.

Suitable transfer agents include mercaptans, cobaloximes, alkylbenzenes such as ethylbenzene, amines such as triethanol amine, halocarbons such as carbon tetrachloride, and the like Suitable emulsifiers include those of the nonionic an anionic types and their mixtures. Suitable nonionic emulsifiers include any of those heretofore employed in emulsion polymerization processes such the alcohol ethoxylates, polyoxyethylene lauryl ethers, polyoxyethylene monostearates, and the like. Similarly, useful anionic emulsifiers include those known to be useful in emulsion polymerization procedures such as the alkali metal sulfonates, sulfates, phosphates and sulfosuccinate surfactants. Specific examples of these surfactants include alkali metal sulforesorcinates; sulfonated glyceryl esters of fatty acids; salts of sulfonated monovalent alcohol esters; sulfonated aromatic hydrocarbon alkali salts such as sodium alpha-naphthalene monosulfonate; sulfates such as sodium lauryl sulfate, sodium cetostearyl sulfate, triethanol amine lauryl sulfate and sodium lauryl ether sulfate; phosphates such as the potassium salts of cetyl phosphate; and, sulfosuccinates such as disodium lauryl sulfosuccinates, anionic surfactants such as cetrimonium chloride, distearyldimethylammonium chloride, lauryl methyl gluceth-10 hydroxypropyldimonium chloride, benzalkonium chloride and zwitterionic surfactants such as cocamidopropyl hydroxysultaine, cocamidopropyl betaine and lecithin.

Suitable stabilizers where utilized include polymeric steric stabilizers such as partially hydrolyzed poly(vinyl acetate), thickeners such as guar gum, cellulose and its derivatives, polyacrylates and polyacrylic acid copolymers.

Suitable co-stabilizers where utilized include polyethers such as ethylene oxide/propylene oxide copolymers, glycols, glycerin and electrolytes such as potassium chloride and calcium chloride.

Water-miscible organic solvents where utilized include, e.g., alcohols and esters and can represent up to 10 weight percent of the aqueous phase.

The free radical initiator can be selected from, for example, azo initiators, inorganic peroxides, organic peroxides and redox initiators. Azo initiators include (2,2-azobis (2-methylpropionamidine) dihydrochloride; inorganic peroxides include ammonium persulfate, sodium persulfate and potassium persulfate; organic peroxides include benzoyl peroxide and dilauroyl peroxide; redox initiators include ammonium persulfates and 2-hydroxy-2 sulfinatoacetic acid disodium salt, hydrogen peroxide and absorbic acid and potassium persulfate and tetramethylethylenediamine. The free radical reaction can also be initiated by high energy sources such as ultrasound and radiation in accordance with conventional and otherwise known procedures.

Particle size of the polymerizate content of the emulsion herein may be effectively controlled by selection and/or adjustment of the viscosity of the polydiorganosiloxane prior to emulsification as well as adjustment of the temperature, mixing speed and/or emulsifier used in preparing the emulsion. In one embodiment, the silicone gel emulsion particle size can be from 10 nm to 100 microns, and in another embodiment from 100 nm to 30 microns.

Depending on the nature of the selected free radical imitator, copolymerization temperatures of from 40° to 100° C. with reaction times of from 1 to 10 hrs are generally suitable for providing the crosslinked polyorganosiloxane O/W gel emulsion of the invention.

Typical properties of the crosslinked polyorganosiloxane O/W gel emulsions of the invention include a crosslink density as measured by durometer and expressed as Type A hardness according to the JIS K6253 standard of from 10 to 90 and preferably from 20 to 80, a storage modulus (G') as measured by rheometry of from 500 to 50,000 Pa, and preferably from 500 to 3,000 Pa, and a maximum swellability as measured by swelling in isopropyl myristate of not greater than 600 wt/wt percent and preferably not greater than 300 wt/wt percent.

Maximum swellability is measured using the following procedure. The gel emulsion is dried and placed in a sealable container, the weight of the dry gel being recorded as w1. Excess isopropyl myristate is added and the weight recorded as w2; the mass of isopropyl myristate is at least 20 times that of the dry gel. The container is sealed and placed in an oven heated to 50° C. oven for 72 hr. The resulting solvent-swollen suspension is filtered through a 0.2 mm screen and the filtered liquid weight is recorded as w3. The maximum swellability is calculated using the following equation.

$$(w2-w3)/w1*100=\text{maximum swellability}$$

The crosslinked polyorganosiloxane O/W gel emulsion of the invention typically exhibits a greater crosslink density, greater storage modulus (G') and/or reduced swellability compared to one or more of these properties of a known type of crosslinked polyorganosiloxane O/W gel emulsion prepared by the hydrosilylation of the same weight amount of polyorganosiloxane reactant(s) possessing the same number of functional groups in the presence of a precious metal hydrosilylation catalyst such as Karstedt's catalyst ("known crosslinked polyorganosiloxane O/W gel emulsion"). For example, the crosslinked polyorganosiloxane O/W gel emulsion of the invention may exhibit a crosslink density as measured by durometer and expressed as Type A hardness according to the JIS K6253 standard that is at least 5, preferably at least 10, and more preferably at least 15 percent greater than that of the comparable known crosslinked polyorganosiloxane O/W gel emulsion; a storage modulus (G') as measured by rheometry that is at least 10, preferably at least 20, and more preferably at least 30 percent greater than that of the known crosslinked polyorganosiloxane O/W gel emulsion; and/or a maximum swellability in isopropyl myristate that is at least 5, preferably at least 10, and more preferably at least 15 percent less than that of the known crosslinked polyorganosiloxane O/W gel emulsion.

Even at modestly increased crosslink density, storage modulus (G') and/or reduced swellability, the crosslinked polyorganosiloxane O/W gel emulsion of this invention and its concentrates may impart appreciably improved sensory properties to personal care compositions containing them, e.g., perceptibly higher cushioning and/or reduced tack, compared with the sensory properties of identical personal care compositions containing an equal amount of comparable known crosslinked polyorganosiloxane.

The crosslinked polyorganosiloxane aqueous gel emulsion herein can be incorporated as is in the formulations of these and other personal care products, e.g., in one embodiment in an amount of from 0.1 to 50 weight percent and in another embodiment, in an amount of from 0.5 to 30 weight percent. However, if desired, the gel emulsion can be further processed, e.g., by drying or by first breaking the emulsion and then drying, to remove at least some of its water and other volatiles, e.g., at least 50, and preferably at least 70, weight percent thereof, thereby concentrating the crosslinked polyorganosiloxane content, the concentrate thereafter being re-swollen employing a solvent or swelling agent such as any of those previously mentioned. The re-swollen crosslinked polyorganosiloxane may then be utilized in the formulation of personal care compositions such as any of the above.

As previously indicated, the crosslinked polyorganosiloxane O/W gel emulsion and any concentrate obtained therefrom is advantageously substantially devoid of precious metals where their incorporation in personal care products is contemplated.

The crosslinked polyorganosiloxane O/W gel emulsion herein and/or its concentrate can advantageously be incorporated in any of numerous types of personal care compositions to which it imparts excellent levels of cushioning and powdery after feel. Included among such personal care compositions are deodorants, antiperspirants, antiperspirant/deodorants, stick and roll-on preparations, skin lotions, moisturizers, toners, cleansing preparations, styling gels, hair dyes, hair color preparations, hair straighteners, nail polish, nail polish remover, sunscreens, anti-aging preparations, lipsticks, lip balms, lip glosses, foundations, face powders, eye liners, eye shadows, blushes, makeup, beauty balms, mascaras, moisturizing preparations, foundations, concealers, body and hand preparations, skin care preparations, face and neck preparations, fragrance preparations, soft focus preparations, night and day skin care preparations, tanning preparations, hand liquids, non-woven preparations for personal care, facial tissue, baby lotions, facial cleansing preparations, hair cuticle coats, gels, foam baths, body washes, scrubbing cleansers, controlled-release personal care preparations, hair shampoos, hair conditioners, hair sprays, skin care moisturizing mists, skin wipes, pore skin wipes, pore cleaners, blemish reducers, skin exfoliators, skin desquamation enhancers, anti-acne preparations, skin towelettes, skin cloths, depilatory preparations, personal care lubricants, nail coloring preparations and drug delivery systems for topically applied therapeutics and medicinals.

In addition to the crosslinked polyorganosiloxane O/W gel emulsion herein and/or concentrate thereof, personal care compositions such as those listed above will typically contain one or more components commonly included in a composition of a particular type in the customary amounts, the compositions being prepared in accordance with procedures that are well known in the art.

A recent approach to covering up the signs of aging involves the use of light-diffusing particles which hide skin imperfections while projecting a natural skin tone. This approach has come to be known as the "soft-focus" effect. The criteria for a light-diffusing particle, which if met would provide the optimum diffusion or soft-focus effect, are set forth in Emmert, "Quantification of the Soft-Focus Effect," Cosmetics and Toiletries, 11, 57-61 (1966). The criteria are as follows: (1) the diffusive particle needs to have minimal light absorption, (2) the diffusive particle needs to have high total light transmission to provide a natural appearance, (3) most of the light transmission needs to be diffuse, so that the light reflected from the skin appears to be evenly distributed, (4) the specular reflection must be minimal so as to minimize luster that would increase the appearance of wrinkles, and (5) the scattered reflection component of the total reflection needs to be high in order to have an even light distribution over the area independent of underlying wrinkles. The crosslinked polyorganosiloxane O/W gel emulsion of this invention and its concentrates have been found to meet these criteria and are therefore advantageously incorporated in personal care compositions for which a soft-focus effect is desired. Such soft-focus compositions may additionally contain one or more conventional or otherwise known soft-focus additives, e.g., boron nitride powders (e.g., Softouch CC6097, Momentive Performance Materials, Inc.), nylon powders (e.g., those available from Vantage Specialty Ingredients, Inc.), silica and fumed alumina powders coated with dimethicone/vinyl dimethicone crosspolymer (e.g., Dow Corning® 9701 Cosmetic Powder and Dow Corning® EP-9293 AL Cosmetic Powder), fumed alumina powders (e.g., SpectrAl®, Cabot Corporation), alumina platelets coated with titanium dioxide (e.g., Spectraflex® Focus Pigments from SunChemical), silica silylate aerogel powders (e.g., those available from Dow Corning), spherical alumina powders, and the like.

The crosslinked polyorganosiloxane O/W gel emulsion and/or concentrate of this invention, alone or in combination with known and conventional soft-focus additives such as those listed above, can be incorporated in personal care compositions for which a soft-focus effect is desired in widely varying amounts, e.g., from 0.2 to 20, preferably from 0.5 to 10, and still more preferably from 1 to 5, weight percent. It is particularly advantageous to employ as a soft-focus effect additive a composition comprising a crosslinked polyorganosiloxane O/W gel emulsion and/or concentrate in accordance with the invention and a known or conventional soft-focus effect material such as any of those aforementioned. Such soft-focus effect compositions have been found to provide comparable or even significantly greater average diffuse transmission levels than those of an equal weight amount of the crosslinked polyorganosiloxane O/W gel emulsion/concentrate component(s). Considering that the crosslinked polyorganosiloxane O/W gel emulsion/concentrate herein tends to be more costly than most known and conventional soft-focus effect additives such as boron nitride, it can be more economical to use a combination of these soft-focus effect materials rather than the emulsion/concentrate alone.

The following examples are illustrative of crosslinked polyorganosiloxanes of the invention, their preparation and various kinds of personal care compositions formulated therewith.

Of the examples presented below illustrating the preparation of crosslinked polyorganosiloxane O/W gel emulsions in accordance with the invention, Examples 1-3 illustrate the copolymerization of an admixture of polyorganosiloxanes I containing free radical polymerizable ethylenically unsaturated groups and no hydrosilyl groups and optional polyorganosiloxane II containing hydrosilyl groups; Example 4 illustrates the polymerization of polyorganosiloxane I containing free radical polymerizable ethylenically unsaturated groups and no hydrosilyl groups; and, Example 5 illustrates the preparation of polyorganosiloxane I containing both free radical polymerizable groups and hydrosilyl groups and its subsequent polymerization. Table I below sets forth the structures of the aforementioned polyorganosilanes I and II:

TABLE 1

Structures of Some Reactive Polyorganosiloxanes

| Example | Polyorganosiloxane I | Polyorganosiloxane II |
|---|---|---|
| 1 | $M^V D^V_{560} D_{36} M^V$ | $M^H D_{20} M^H$ |
| 2 | $M^V D_{200} M^V$ | $M^H_8 Q_4$ |
| 3 | $M^V_8 Q_4$ | $M^H D_{200} M^H$ |
| 4 | $M^V D^V_{560} D_{36} M^V$ | $M^V M^H$ |
| 5 | $M^H D_{10} D^V_{228} M^H$ | $D^V D^H D_2$ |

Example 1

A mixture of 40 parts of weight of vinyl polydimethylsiloxane having a viscosity of about 5 Pa·s at 25° C., 10 parts of weight bis-hydrogen dimethicone having a viscosity of about 0.02 Pa·s at 25° C. and 20 parts by weight of isododecane is mixed well and then combined with an admixture of 5 parts of weight polyoxyethylene lauryl ether, and 0.5 parts by weight sodium cetearyl sulfate and 5 parts by weight deionized water in a blender to provide a stable emulsion. Addition of deionized water to the emulsion decreased its crosslinked polyorganosiloxane content to 40 percent by weight. The emulsion was then heated to 60° C. and adjusted to pH 4, followed by the addition of 0.05 parts by weight ammonium persulfate to commence free radical polymerization of the vinyl polydimethysiloxane and its hydrosilylation by the bis-hydrogen dimethicone. After 4 hours, unreacted SiH in the resulting stable O/W emulsion gel was found to be less than 0.1 cc/g when measured by the fermentation tube method described in Luo et al., "Silicone Resin and its Application", Chemical Industry Press, Beijing, pp. 227-228 (2002). The emulsion was adjusted to pH 7 with triethanolamine and 0.8 parts by weight of phenoxyethanol was added thereto as a preservative.

Example 2

A mixture of 50 parts by weight of vinyl polydimethylsiloxane having a viscosity of about 2 Pa·s at 25° C., 10 parts by weight hydrosilyl group-containing polyorganosiloxane having a viscosity of 0.01 Pa·s at 25° C., 5 parts by weight cetearyl methicone having a viscosity of about 0.003 Pa·s at 25° C. and 80 parts by weight dimethicone having a viscosity of about 0.01 Pa·s at 25° C. is blended at 50° C. and thereafter combined with an admixture of 1.5 parts by weight sodium cetostearyl sulfate, 6 parts by weight polyoxyethylene lauryl ether, 8 parts by weight polyoxyethylene monostearate and 30 weight parts deionized water in a blender to provide a stable emulsion. Further addition of deionized water to the emulsion decreased its crosslinked polyorganosiloxane content to 50 percent by weight. The emulsion was heated to 40° C. and adjusted to a pH of 4 followed by the addition thereto of 0.1 parts by weight each of hydrogen peroxide and ascorbic acid to commence free radical polymerization of the vinyl polydimethylsiloxane and its hydrosilylation by the hydrosilyl group-containing polyorganosiloxane. After 4 hours, unreacted SiH in the emulsion was found to be less than 0.1 cc/g when measured by the fermentation tube method. Sodium benzoate, 0.5 parts by weight, was added to the emulsion as a preservative.

The storage moduli (G') of the O/W gel emulsions of Examples 1 and 2, supra, and that of a known type of O/W gel emulsion prepared by hydrosilylation employing Karstedt's catalyst were determined employing conventional G' measurement procedures. G' provides an indication of the cushioning feel of an O/W gel emulsion such that the greater the measured G', the greater the cushioning feel of the emulsion.

The G' measurement data are graphically set forth in FIG. 1. As these data show, the O/W gel emulsions of Examples 1 and 2 illustrating the invention were both significantly higher than that of the known type of O/W gel emulsion therefore indicating a greater degree of cushioning for the crosslinked polyorganosiloxane emulsions herein.

Example 3

A mixture of 100 parts by weight of vinyl polydimethylsiloxane resin having a viscosity of about 0.5 Pa·s at 25° C., 20 parts by weight methylhydrogenpolyorganosiloxane having a viscosity of about 0.2 Pa·s at 25° C., 20 parts by weight isopropyl myristate and 1 part by weight benzoyl peroxide at 60° C. was combined with a mixture of 6 parts by weight steareth-2 and 4 parts by weight steareth-21, 8 parts by weight polyoxyethylene monostearate and 30 parts by weight deionized water in a blender to provide a stable emulsion of the polyorganosiloxanes. Further addition of deionized water to the emulsion reduced its crosslinked polyorganosiloxane content to 50 percent by weight. The emulsion was then heated to 80° C. to commence free radical polymerization/hydrosilylation which was completed in 4 hours. SiH was found to be less than 0.1 cc/g when measured by the fermentation tube method. Following adjustment of the pH to 7, 0.8 parts by weight of phenoxyethanol was added to the crosslinked polyorganosiloxane O/W stable emulsion as a preservative.

Example 4

A mixture of 30 parts by weight vinyl polydimethylsiloxane having a viscosity of about 5 Pa·s at 25° C., 10 parts by weight of isododecane and 10 parts by weight dimethicone having a viscosity of about 1 Pa·s at 25° C. was combined with a mixture of 5 parts by weight polyoxyethylene lauryl ether, 0.5 parts by weight sodium cetearyl sulfate and 5 parts by weight deionized water in a blender to provide a stable emulsion. Further addition of deionized water to the emulsion decreased its crosslinked polyorganosiloxane content to 30 percent by weight. The emulsion was then heated to 60° C. and adjusted to pH 4 followed by the addition of 0.05 parts by weight ammonium persulfate to commence free radical polymerization of the vinyl polydimethylsiloxane. After 4 hours, the pH of the resulting crosslinked polyorganosiloxane stable O/W emulsion was adjusted to 7 with triethanolamine and 0.8 parts by weight of phenoxyethanol added thereto as a preservative.

The D4 and D5 contents (octamethylcyclotetrasiloxane and decamethylcyclopentasiloxane contents, respectively) of the crosslinked polyorganosiloxanes of Examples 1-4, supra, were measured by conventional gas chromatography (GC). The results of the measurements are set forth below in Table 2. In general, it is advantageous to provide an O/W gel emulsion in which the total D4 and D5 content of its crosslinked polyorganosilane component is less than 1,000 ppm.

TABLE 2

D4 and D5 Contents of Crosslinked Polyorganosiloxanes

| Crosslinked Polyorgano-siloxane Gel Emulsion | D4 content (Wt. %, by GC) | D5 content (Wt. %, by GC) |
| --- | --- | --- |
| Example 1 | 0.021 | 0.032 |
| Example 2 | 0.023 | 0.034 |
| Example 3 | 0.023 | 0.033 |
| Example 4 | 0.023 | 0.036 |

Example 5

Polyorganosiloxane I having vinyl groups and hydrosilyl groups was prepared as follows: a mixture of 700 parts by weight 1, 3, 5, 7-tetramethyl-1, 3, 5, 7-tetravinyl tetramethylcyclotetrasiloxane and 30 parts by weight if bis-hydrogen dimethicone having a viscosity of about 0.001 Pa·s at 25° C. was mixed with 1 part acid diatomite at 80° C. for 12 hours. The crosslinkable polyorganosiloxane reaction product, which was filtered to remove acid diatomite, had a viscosity of about 0.2 Pa·s at 25° C.

A mixture of 30 parts by weight of the foregoing crosslinkable polyorganosiloxane, 10 parts by weight isododecane and 20 parts by weight dimethicone having a viscosity of about 3 Pa·s at 25° C. was combined in a blender with a mixture of 5 parts by weight polyoxyethylene lauryl ether, 0.5 parts by weight of sodium cetearyl sulfate and 5 parts by weight deionized water to provide a stable emulsion of the polyorganosiloxane. Further addition of deionized water to the emulsion reduced its crosslinked polyorganosiloxane content to 30 percent by weight. The emulsion was then heated to 60° C. and following adjustment to pH 4, 0.1 parts by weight each of hydrogen peroxide and ascorbic acid were added thereto to commence free radical polymerization/hydrosilylation. Polymerization was completed in 4 hours. SiH as measured by the fermentation tube method was less than 0.1 cc/g. Sodium benzoate, 0.5 parts by weight, was added to the crosslinked polyorganosiloxane O/W emulsion as a preservative.

Example 6

This example illustrates a procedure for concentrating the crosslinked polyorganosiloxane component of the O/W gel emulsion of Example 2 and re-swelling the resulting concentrate in a swelling agent.

50 parts by weight of the crosslinked polyorganosiloxane O/W gel emulsion of Example 2 was heated to 80° C. for 8 hours thereby reducing its water by over 80 weight percent. The thus-dried gel was combined with an equal weight amount of dimethicone having a viscosity of about 0.0005 Pa·s at 25° C. in a blender at about 300-500 rpm at ambient temperature over 1-3 hours to re-swell the crosslinked polymer concentrate.

Examples 7-13

Examples 7-13 illustrate various personal care compositions formulated with a crosslinked polyorganosiloxane O/W gel emulsion of the invention.

Example 7: Soft-focus Effect Whitening Moist Facial Mask

| No. | Component | Wt % |
| --- | --- | --- |
| Part A | | |
| 1 | crosslinked polyorgansiloxane gel emulsion of Example 2 | 5.00 |
| 2 | dimethicone and hydrogenated polyisobutene* | 0.30 |
| 3 | phenoxyethanol | 0.50 |
| 4 | sodium benzoate | 0.50 |
| 5 | citric acid | 0.20 |
| 6 | fragrance | 0.10 |
| Part B | | |
| 7 | boron nitride | 0.50 |
| 8 | glycerine | 5.00 |
| 9 | xanthan gum | 0.10 |
| 10 | carpobol 981 | 0.15 |
| 11 | triethanolamine | 0.15 |
| 12 | DI water | to 100 |

*Momentive Performance Materials

Procedure:
1. Blend Part A components.
2. Pre-mix components 7 and 8 and blend with remaining Part B components. Blend mixture of Parts A and B.

Physical Properties and Stability Data:
1. Viscosity: 4000 cps 2. pH: 6.6
3. 48° C. Oven Test for 4 weeks—stable.
4. Freeze-Thaw Stability Test for 2 cycles—stable.

| Example 8: Soft-focus Effect Powdery Facial Lotion Spray | | | |
|---|---|---|---|
| | Component | | Wt % |
| Part A | | | |
| 1 | crosslinked polyorganosiloxane gel emulsion of Example 2 | | 5.00 |
| 2 | dimethicone and hydrogenated polyisobutene * | | 0.30 |
| 3 | phenoxyethanol | | 0.80 |
| 4 | sodium benzoate | | 0.50 |
| 5 | citric acid | | 0.20 |
| 6 | fragrance | | 0.10 |
| Part B | | | |
| 7 | butylene glycol | | 5.00 |
| 8 | boron nitride | | 0.50 |
| 9 | microcrystalline cellulose, cellulose gum | | 2.00 |
| 10 | DI water | | to 100 |

* Momentive Performance Materials Inc.

Procedure:
1. Partly mix components 7 and 8 to provide a pre-mix.
2. Disperse component 9 in remaining component 7 until uniform and add water. Homogenize for 10 min.
3. Add Part A and remaining component 8 to Part B under stirring until a homogeneous A+B blend is obtained.

Physical Properties and Stability Data:
1. pH: 6.6
2. 48° C. Oven Test for 4 weeks—stable.
3. Freeze-Thaw Stability for Test 2 cycles—stable.

| Example 9: Sunscreen Lotion | | |
|---|---|---|
| No. | Component | wt % |
| Part A | | |
| 1 | glycerine | 3 |
| 2 | EDTA-2Na | 0.05 |
| 3 | propylene glycol | 6 |
| 4 | carbopol | 0.15 |
| 5 | crosslinked polyorganosiloxane gel emulsion of Example 3 | 5 |
| 6 | DI water | to 100 |
| Part B | | |
| 7 | steareth-2 | 2 |
| 8 | steareth-21 | 1.5 |
| 9 | polymethylsilsesquioxane* | 3 |
| 10 | dimethicone and trimethylsiloxysilicate* | 4 |
| 11 | caprylyl methicone* | 3 |
| 12 | cyclopentasiloxane* | 5 |
| 13 | diethyl amino hydroxybenzoyl hexyl benzoate | 1 |
| 14 | octyl methoxycinnamate | 6.4 |
| 15 | titanium oxide | 2.7 |
| Part C | | |
| 16 | chamomile extract | 0.04 |
| 17 | triethanolamine | 0.15 |
| 18 | dipotassium glycyrrhizate | 0.15 |
| 19 | fragrance | 0.2 |
| 20 | phenoxyethanol | 0.5 |
| 21 | sodium benzoate | 0.5 |
| 22 | citric acid | 0.2 |

*Momentive Performance Materials Inc.

Procedure
1. Mix Part A and heat to 80° C.
2. Mix Part A and heat to 80° C.; slowly add Part A to Part B.

3. Mix Part C and add to A+B mixture. Homogenize A+B+C mixture briefly and stir.

Stability Test:
1. 45° C. Oven Test for one month—stable.
2. −18° C. Storage Test for one month—stable.
3. Freeze-thaw Stability Test for 3 cycles—stable.

| Example 10: Body Wash | | | |
|---|---|---|---|
| No. | Component | | Wt % |
| Part A | | | |
| 1 | sodium laureth sulfate (70%) | | 13 |
| 2 | cocamidopropyl betaine (30%) | | 9 |
| 3 | sodium lauroyl Oat [?] amino acids (30%) | | 8 |
| 4 | DI water | | to 100 |
| Part B | | | |
| 5 | DI water | | 10.00 |
| 6 | polyquaternium-10 | | 0.30 |
| Part C | | | |
| 7 | triethanolamine | | 0.15 |
| 8 | phenoxyethanol | | 0.50 |
| 9 | sodium benzoate | | 0.50 |
| 10 | citric acid | | 0.20 |
| 11 | sodium chloride | | q.s. |
| 12 | fragrance | | q.s. |
| 13 | pigment | | q.s. |
| 14 | crosslinked polyorganosiloxane gel emulsion of Example 1 | | 3~5 |

Procedure:
1. Pre-mix components 1 and 2 and blend with other components of Part A. Heat to 75° C.
2. Blend components of Part B and heat to 75° C. Blend Parts A and B.
3. Cool A+B mixture to 45° C. and add Part C thereto under stirring.

| Example 11: Mousse Moisturizing Concentrate | | | |
|---|---|---|---|
| No. | Component | | Wt % |
| Part A | | | |
| 1 | cyclopentasiloxane* | | 2.00 |
| 2 | dimethicone and hydrogenated polyisobutene* | | 0.70 |
| 3 | hydroxyethyl acrylate and sodium acryloyldimethyl taurate copolymer | | 1.20 |
| Part B | | | |
| 4 | crosslinked polyorganosiloxane gel emulsion of Example 4 | | 2.00 |
| 5 | phenoxyethanol | | 0.50 |
| 6 | sodium benzoate | | 0.50 |
| 7 | citric acid | | 0.20 |
| 8 | fragrance | | 0.10 |
| 9 | pigment | | q.s. |
| 10 | DI water | | to 100 |

Procedure:
1. Blend components of Part A.
2. Add Part B components in sequence to Part A.

Physical Properties and Stability Data:
1. Viscosity: 10000 cps.
2. pH: 6.6
3. 48° C. Oven Test for 4 weeks—stable.
4. Freeze-Thaw Stability Test for 2 cycles—stable.

Example 12: Velvety Leave-on Conditioner

| No. | Component | wt % |
|---|---|---|
| Part A | | |
| 1 | hydroxyethylcellulose, 2% | 10.00 |
| 2 | polyquaternium-37, mineral oil and laureth-6 | 1.50 |
| 3 | crosslinked polyorganosiloxane gel emulsion of Example 1 | 3~5.00 |
| 4 | DI water | to 100 |
| Part B | | |
| 5 | dimethicone* | 2.00 |
| 6 | cyclopentasiloxane* | 5.00 |
| 7 | PEO(20) sobitan monolaurate | 0.50 |
| Part C | | |
| 8 | fragrance | q.s. |
| 9 | phenoxyethanol | 0.50 |
| 10 | sodium benzoate | 0.50 |
| 11 | citric acid | 0.20 |

*Momentive Performance Materials Inc.

Procedure:
1. Mix components of Part A.
2. Mix components of Part B.
3. Add Part B to Part A under stirring.
4. Add Part C to A+B mixture under stirring.

Example 13: Shampoo

| No. | Component | wt % |
|---|---|---|
| Part A | | |
| 1 | carbopol | 0.2 |
| 2 | EDTA | 0.05 |
| 3 | sodium laureth sulfate (70%) | 20.00 |
| 4 | sodium lauryl sulfate | 0.50 |
| 5 | coconut monoethanol amide | 1.2 |
| 6 | glycol distearate/glycol monostearate (pearlizing agent) | 1.5 |
| 7 | cocamidopropyl betaine | 5.00 |
| 8 | cetearyl alcohol | 0.3 |
| 9 | DI water | to 100 |
| Part B | | |
| 10 | guarhydroxylpropyltrimoniumchloride | 0.30 |
| 11 | DI water | 10.00 |
| Part C | | |
| 12 | triethanolamine | 0.15 |
| 13 | phenoxyethanol | 0.50 |
| 14 | sodium benzoate | 0.50 |
| 15 | citric acid | 0.20 |
| 16 | sodium chloride | q.s. |
| 17 | fragrance | q.s. |
| 18 | pigment | q.s. |
| 19 | crosslinked polyorganosiloxane gel emulsion of Example 1 | 3~5 |

Procedure:
1. Pre-mix 1 and 2, blend with other components of Part A and heat to 80° C.;
2. Blend components of Part B and heat to 80° C. Combine Parts A and B.
3. Cool to 45° C. and add Part C to Part A+B under stirring.

Example 14: Sunscreen

| No. | Component | wt % |
|---|---|---|
| Part A | | |
| 1 | cyclopentasiloxane and PEG/PPG-20/15 dimethicone[1] | 1.00 |
| 2 | cetyl alcohol | 1.00 |
| 3 | C30-45 alkyl cetearyl dimethicone | 2.00 |
| 4 | caprylyl methicone[1] | 2.00 |
| 5 | caprylic/capric triglyceride | 3.00 |
| 6 | octyl methoxycnnamate | 4.00 |
| 7 | phenyl dimethicone[1] | 1.00 |
| Part B | | |
| 8 | synthetic wax and iron oxides (C.I. 77492) and isopropyl[2] | 0.34 |
| 9 | titanium dioxide, hydrogenated polyisobutene, trimethoxycaprylylsilane, hydrogenated castor oil and hydroxystearate PPG-5-ceteth-10 phosphate[3] | 3.60 |
| Part C | | |
| 10 | titanium dioxide, alumina and methicone[2] | 5.00 |
| 11 | dimethicone/methicone copolymer and talc[4] | 7.00 |
| Part D | | |
| 12 | dimethicone and cetearyl dimethicone crosspolymer[1] | 35.00 |
| 13 | crosslinked gel concentrate of Example 6 | 35.00 |
| Part E | | |
| 14 | fragrance | q.s. |
| 15 | preservative | q.s. |

[1]Momentive Performance Materials Inc.
[2]Kobo Products Inc.
[3]Sentient Cosmetic Technologies
[4]Daito Kasei Kogyo Co., Ltd.

Procedure:
1. Heat Part A to 70-75° C. and mix until homogeneous.
2. Add Part B to Part A and homogenize A+B mixture.
3. Add Part C to A+B mixture and homogenize A+B+C mixture.
4. Add Part D to A+B+C mixture and homogenize A+B+C+D mixture until homogeneous.
5. Cool A+B+C+D mixture to 40-45° C., add Part E thereto and mix well.

Examples 15-21

Comparative Examples 1 and 2

Table 3 below sets forth the formulation of several skin cream compositions prepared with ammonium acryloyldimethyltaurate/vinyl pyrrolidone copolymer aqueous thickener (Aristoflex, Clariant). Examples 15-21 demonstrate the soft-focus (light diffusion) effect of the crosslinked polyorganosiloxane O/W gel emulsion of Example 1 with Examples 16, 20 and 21 demonstrating the soft-focus effect of a combination of this emulsion and a boron nitride powder (Softouch CC9097, Momentive Performance Materials, Inc.). Comparative Example 1 is provided as a control skin cream formulation and therefore contains no soft-focus effect additive. Comparative Example 2 demonstrates the soft-focus effect of a mixture of caprylyl methicone and C30-45 alkyl cetearyl dimethicone (Velvesil 034, Momentive Performance Materials, Inc.) and an emulsifier PEG-8 dimethicone (Silsoft 840, Momentive Performance Materials, Inc.).

The skin cream of comparative Example 2 and Examples 15-21 were prepared by dispersing the indicated soft-focus additive within the balance of each formulation.

Each skin cream formulation was applied to a clear transparency using a 8 mil bird applicator. The films were dried overnight in an oven at 45° C.

The optical properties of each sample were measured using a X-Rite Color-Eye 7000A spectrophotogoniometer. Two kinds of measurement were taken for each skin formulation: total transmission and specular transmission. A third measurement, diffuse transmission, was obtained by calculating the difference between the total transmission and the specular transmission and is reported as a percent of total transmission, the greater the increase in diffuse transmission, the greater the soft-focus effect.

TABLE 3

Light-diffusing Properties of Soft-focus Effect Additives in Skin Creams (all amounts of components in weight percent)

| Component | Comp. Ex. 1 | Comp. Ex. 2 | Ex. 15 | Ex. 16 | Ex. 17 | Ex. 18 | Ex. 19 | Ex. 20 | Ex. 21 |
|---|---|---|---|---|---|---|---|---|---|
| ammonium acryloyidimethyltaurate/VP copolymer | 1 | 1 | 1 | 1 | 1 | 1 | 1 | 1 | 1 |
| crosslinked polyorganosiloxane O/W gel emulsion of Example 1 | | | 1.25 | 1.14 | 2.5 | 5 | 10 | 2.28 | 4.55 |
| mixture of caprylyl methicone and C30-45 alkyl cetearyl dimethicone PEG80-dimethicone | | 10 | | | | | | | |
| boron nitride | | | | 0.11 | | | | 0.22 | 0.45 |
| water | 99 | 87 | 97.75 | 97.75 | 96.5 | 94 | 89 | 96.5 | 94 |
| Optical Properties of the Skin Creams | | | | | | | | | |
| Average Total Transmission % | 90 | 91 | 89 | 88 | 90 | 89 | 87 | 86 | 80 |
| Average Specular Transmission % | 88 | 44 | 54 | 43 | 26 | 14 | 8 | 29 | 13 |
| Average Diffuse Transmission % | 2 | 52 | 39 | 51 | 71 | 84 | 90 | 86 | 84 |

As the data in Table 3 show, and as expected, the skin cream of Comparative Example 1 showed only a negligible increase in average diffuse transmission (2%) thus serving as a suitable control for the skin creams of Comparative Example 2 and Examples 15-21.

The skin cream of Comparative Example 2 illustrating a soft-focus additive outside the scope of the invention and present therein at 10 weight percent showed a significant increase in average diffuse transmission (52%) over that of Comparative Example 1. While the skin cream of Example 15 containing the crosslinked polyorganosiloxane O/W gel emulsion of Example 1 as its sole soft-focus additive resulted in an increase in average diffuse transmission which was 75% of that Comparative Example 2, it accomplished this with a far smaller amount of such additive (1.25 weight percent compared to 10 weight percent). The skin cream of Example 19 containing the crosslinked polyorganosiloxane O/W gel emulsion of Example 1 at 10 weight percent showed a far higher increase in average diffuse transmission than that of Comparative Example 2 containing the same amount of soft-focus additive. The skin creams of Examples 17 and 18 containing much less soft-focus additive of this invention compared to that of the skin cream of Comparative Example 2 both showed increases in average diffuse transmission that are considerably higher than that of the skin cream of Comparative Example 2.

The skin creams of Examples 16, 20 and 21 illustrating the use of a soft-focus effect composition containing the crosslinked polyorganosiloxane O/W gel emulsion of Example 1 in combination with a boron nitride powder show that comparable or increased levels of average diffuse transmission can be achieved by replacing a portion of the crosslinked polyorganosiloxane O/W gel emulsion present in the skin creams of Examples 15, 17 and 18 with boron nitride.

While the disclosure has been described with reference to a preferred embodiment, it will be understood by those skilled in the art that various changes may be made and equivalents may be substituted for elements thereof without departing from the scope of the disclosure. In addition, many modifications may be made to adapt a particular situation or material to the teachings of the disclosure without departing from essential scope thereof. Therefore, it is intended that the disclosure not be limited to the particular embodiment disclosed as the best mode contemplated for carrying out this disclosure, but that the disclosure will include all embodiments falling within the scope of the appended claims.

The invention claimed is:

1. A personal care composition comprising at least one O/W gel emulsion of crosslinked polyorganosiloxane which comprises at least one member selected from the group consisting of (a) crosslinked polyorganosiloxane O/W gel emulsion obtained from the free radical-initiated addition polymerization under emulsion polymerization reactions conditions of polyorganosiloxane I containing ≥2 free radical polymerizable groups and 0 or ≥1 hydrosilyl group(s) and, optionally, polyorganosiloxane II containing 0 or 1 free radical polymerizable group and ≥1 hydrosilyl group(s), (b) crosslinked polyorganosiloxane O/W gel emulsion (a) which is substantially devoid of precious metal, (c) concentrate of crosslinked polyorganosiloxane (a), and (d) concentrate of crosslinked polyorganosiloxane O/W gel emulsion (b), and wherein polyorganosiloxane I consists of the general formula I:

$$M_a M^H_b M^V_c M''_d M^*_e D_f D^H_g D^V_h D''_i D^*_j T_k T^H_l T^V_m T''_n T^*_o Q_p \quad \text{I}$$

wherein
$M = R^1 R^2 R^3 SiO_{1/2}$;
$M^H = R^4 R^5 HSiO_{1/2}$;
$M^V = R^6 R^7 R^8 SiO_{1/2}$;
$M'' = R^9 R^{10} R^{22} SiO_{1/2}$;
$M^* = R^{11} R^{12} R^{23} SiO_{1/2}$;
$D = R^{13} R^{14} SiO_{2/2}$
$D^H = R^{15} HSiO_{2/2}$;
$D^V = R^{16} R^{17} SiO_{2/2}$;
$D'' = R^{18} R^{22} SiO_{2/2}$;

D*=R$^{19}$R$^{23}$SiO$_{2/2}$;
T=R$^{20}$SiO$_{3/2}$;
T$^H$=HSiO$_{3/2}$;
T$^V$=R$^{21}$SiO$_{3/2}$;
T"=R$^{22}$SiO$_{3/2}$;
T*=R$^{23}$SiO$_{3/2}$; and,
Q=SiO$_{4/2}$ in which R$^1$, R$^2$, R$^3$, R$^4$, R$^5$, R$^7$, R$^8$, R$^{13}$, R$^{14}$, R$^{15}$, R$^{17}$ and R$^{20}$ each independently is a monovalent hydrocarbon group of up to 60 carbon atoms; R$^6$, R$^{16}$ and R$^{21}$ each independently is a free radical polymerizable group; R$^9$, R$^{10}$ and R$^{18}$ each independently is a monovalent hydrocarbon group of up to 60 carbon atoms or R$^{22}$; each R$^{22}$ independently is a monovalent alkoxy group of up to 60 carbon atoms; R$^{11}$, R$^{12}$ and R$^{19}$ each independently is a monovalent hydrocarbon group of up to 60 carbon atoms, or R$^{23}$; each R$^{23}$ independently is a divalent alkylene group R$^{24}$ of from 3 to 6 carbon atoms to which is bonded one or more alkyleneoxy groups having a total of from 2 to 200 carbon atoms containing one or more ether moieties; and, subscripts a, b, c, d, e, f, g, h, i, j, k, l, m, n, o and p each independently is 0 or a positive number subject to the provision that c+h+m≥2; and, polyorganosiloxane II is defined the same as for polyorganosiloxane I but with the limitation in polyorganosiloxane II that c+h+m is 0 or 1 and b+g+l≥1, and subject to this limitation, each of groups R$^1$-R$^{24}$ and subscripts a-p of polyorganosiloxane II are selected independently of groups R$^1$-R$^{24}$ and subscripts a-p of polyorganosiloxane I.

2. The personal care composition of claim 1 wherein at least one of free radical polymerizable groups R$^6$, R$^{16}$ and R$^{21}$ of polyorganosiloxane I is selected from the group consisting of:

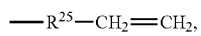  I(a)

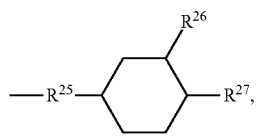  I(b)

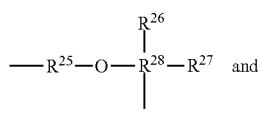  I(c)

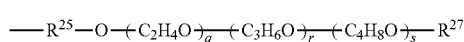  I(d)

in which each R$^{25}$ independently is a divalent hydrocarbon group of up to 20 carbon atoms, optionally containing one or more heteroatoms; R$^{26}$ and R$^{27}$ each independently is an ethylenically unsaturated free radical polymerizable group; R$^{28}$ is a trivalent hydrocarbon group of up to 20 carbon atoms, optionally containing one or more heteroatoms; and, subscripts q, r and s each independently is 0 or a positive number subject to the limitation that q+r+s≥1.

3. The personal care composition of claim 2 wherein at least one of R$^{26}$ and R$^{27}$ of polyorganosiloxane I and/or polyorganosiloxane II is selected to be:

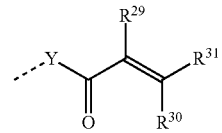

in which Y is absent or is an R$^{25}$ group as previously defined and R$^{29}$, R$^{30}$ and R$^{31}$ each independently is hydrogen or a monovalent hydrocarbon group of up to 20 carbon atoms.

4. The personal care composition of claim 1 wherein polyorganosiloxane I is at least one member selected from the group consisting of:

  I(e)

wherein M$^V$, D, D$^V$ and M are as previously defined and subscripts c, f and h are 0 or a positive number subject to the limitation that f is 0 to 2000, h is 0 to 500, c is 0 to 2 and c+h is 2 to 500;

  I(f)

wherein M$^V$, D, D$^V$ and M are as previously defined and subscripts c, f and h are 0 or a positive number subject to the limitation that f is 0 to 2000, h is 0 to 500, c is 0 to 50 and c+h is 2 to 500;

  I(g)

wherein M$^V$, and Q are as previously defined and subscripts c and p are 0 or a positive number subject to the limitation that c is ≥1, p is ≥1 and c+p is 2 to 100; and,

  I(h)

wherein M$^H$, M$^V$, D, D$^H$, D$^V$ and M are as defined and b, c, f, g and h are 0 or a positive number subject to the limitation that f is 1 to 1000, b is 0 or 1, c is 0 to 2, b+g is 1 and c+h is 2 to 500; and,

  I(i)

wherein D and D$^V$ are as previously defined and subscripts f and h are 0 or a positive number subject to the limitation that f+h is 3 to 8.

5. The personal care composition of claim 4 wherein:
in polyorganosiloxane I(e), f is 10 to 1000, h is 0 to 100, c+h is 2 to 100 and each M$^V$ and D$^V$ moiety independently contains a vinyl, allyl, methallyl, acrylate and/or alkacrylate group;
in polyorganosiloxane I(f), f is 10 to 1000, h is 0 to 100, c is 0 to 50, c+h is 2 to 100 and each M$^V$ and D$^V$ moiety independently contains a vinyl, allyl, methallyl, acrylate and/or alkacrylate group;
in polyorganosiloxane I(g), c is ≥2, p is ≥2, and c+p is 4 to 40 and each M$^V$ and D$^V$ moiety independently contains a vinyl, methallyl, acrylate and/or alkacrylate group;
in polyorganosiloxane I(h), f is 10 to 300, c+h is 2 to 100 and each M$^V$ and D$^V$ moiety independently contains a vinyl, allyl, methallyl, acrylate and/or alkacrylate group; and,
in polyorganosiloxane I(i), f+h is 3 to 6 and each D$^V$ moiety independently contains a vinyl, allyl, methallyl, acrylate and/or alkacrylate group.

6. The personal care composition of claim 4 wherein:
in polyorganosiloxane I(e), f is 10 to 500, h is 0 to 50, c+h is 2 to 10 and each M$^V$ and D$^V$ moiety contains a vinyl group;

in polyorganosiloxane I(f), f is 10 to 500 and c+h is 2 to 50 and each $M^V$ and $D^V$ moiety contains a vinyl group;

in polyorganosiloxane I(g), c is 3, p is ≥3, and c+p is 6 to 20 and each $M^V$ moiety contains a vinyl group;

in polyorganosiloxane I(h), f is 10 to 100, c+h is 2 to 50 and each $M^V$ and $D^V$ moiety contains a vinyl group; and, in polyorganosiloxane I(i), f+h is 3 to 5 and each $D^V$ moiety contains a vinyl group.

7. The personal care composition of claim 1 wherein polyorganosiloxane II is at least one member selected from the group consisting of:

$$M^H{}_b D_f D^H{}_g M_{2-b} \qquad \text{II(a)}$$

wherein $M^H$, D, $D^H$ and M' are as previously defined and b, f and g are 0 or a positive number subject to the limitation that f is 10 to 300, g is 0 to 50, b is 0 to 2 and b+g is 1 to 100;

$$M^H{}_b D_f D^H{}_g D^*{}_j M_{2-b} \qquad \text{II(b)}$$

wherein $M^H$, D, D*, $D^H$ and M are as previously defined and subscripts b, f, g and j are zero or a positive number subject to the limitation that b is 0 to 2, g is from 0 to 50, j is 0.1 to 10, f is 0 to 500, and b+g is 1 to 100;

$$M^H{}_b Q_p M_{2-b} \qquad \text{II(c)}$$

wherein $M^H$, Q and M are as previously defined and b and p are 0 or a positive number subject to the limitation that b is ≥1, p is ≥1 and b+p is 2 to 40; and,

$$M^H{}_b D_f D''{}_i D^H{}_g M_{2-b} \qquad \text{II(d)}$$

wherein $M^H$, D, D'', $D^H$ and M are as previously defined and b f, I and g are 0 or a positive number subject to the limitations that f is 10 to 50, i is 0 to 20 and b+g is 1 to 100;

$$M^H{}_b M^V{}_c D_f D^H{}_g D^V{}_h M_{2-b} \qquad \text{II(e)}$$

wherein $M^H$, $M^V$, D, $D^H$ and M are as previously defined and b, c, f, g and h are 0 or a positive number subject to the limitation that f is 1 to 300, b+g is ≥1 and c+h is 1 to 100; and,

$$D_f D^H{}_g D^V{}_h \qquad \text{II(f)}$$

wherein D, $D^H$ and $D^V$ are as previously defined and f, g and h are 0 or a positive number subject to the limitation that f+g+h is 3 to 7.

8. The personal care composition of claim 7 wherein:

in polyorganosiloxane II(a), f is 10 to 30, g is 1 to 30 and b+g is 1 to 32;

in polyorganosiloxane II(b), g is 1 to 30, j is 0.1 to 8, f is 10 to 150 and b+g is 1 to 32;

in polyorganosiloxane II(c), b is ≥3, p is ≥3, and b+p is 6 to 20;

in polyorganosiloxane II(d), f is 10 to 40, i is 1 to 8 and b+g is 1 to 14;

in polyorganosiloxane II(e), f is 10 to 30, b+g is ≥2 and c+h is 0 or 1; and, in polyorganosiloxane II(f), f+g+h is 3 to 6.

9. The personal care composition of claim 7 wherein:

in polyorganosiloxane II(a), f is 10 to 25, g is 2 to 10 and b+g is 2 to 12;

in polyorganosiloxane II(b), g is 2 to 10, j s 0.1 to 6 and f is 10 to 125; and b+g is 2 to 20;

in polyorganosiloxane II(c), b is ≥3, p is ≥3 and b+p is 6 to 18;

in polyorganosiloxane II(d), f is 10 to 35 and b+g is 1 to 10;

in polyorganosiloxane II(e), f is 10 to 24 and b+g ≥3; and, in polyorganosiloxane II(f)f+g+h is 3 to 5 and $D^V$ where present contains a vinyl group.

10. The personal care composition of claim 1 selected from the group consisting of deodorants, antiperspirants, antiperspirant/deodorants, stick and roll-on preparations, skin lotions, moisturizers, toners, cleansing preparations, styling gels, hair dyes, hair color preparations, hair straighteners, nail polish, nail polish remover, sunscreens, anti-aging preparations, lipsticks, lip balms, lip glosses, foundations, face powders, eye liners, eye shadows, blushes, makeup, beauty balms, mascaras, moisturizing preparations, foundations, concealers, body and hand preparations, skin care preparations, face and neck preparations, fragrance preparations, soft focus preparations, night and day skin care preparations, tanning preparations, hand liquids, non-woven preparations for personal care, facial tissue, baby lotions, facial cleansing preparations hair cuticle coats, gels, foam baths, body washes, scrubbing cleansers, controlled-release personal care preparations, hair shampoos, hair conditioners, hair sprays, skin care moisturizing mists, skin wipes, pore skin wipes, pore cleaners, blemish reducers, skin exfoliators, skin desquamation enhancers, anti-acne preparations, skin towelettes, skin cloths, depilatory preparations, personal care lubricants, nail coloring preparations and drug delivery systems for topically applied therapeutics and medicinals.

11. A soft-focus effect composition comprising the personal care composition of claim 1 and at least one other soft-focus effect additive.

12. A soft focus composition exhibiting a soft-focus effect comprising a soft-focus effect-imparting amount of the soft-focus effect composition of claim 11.

13. The personal care composition of claim 1 wherein at least one of (a)-(d) is produced by a process which employs a free radical initiator and wherein the a free radical initiator is selected from the group consisting of azo initiators, inorganic peroxides, organic peroxides, and redox initiators.

14. The personal care composition of claim 1, wherein the subscripts a, b, d and e are zero.

* * * * *